(12) United States Patent
Bernardelli

(10) Patent No.: US 6,689,881 B1
(45) Date of Patent: Feb. 10, 2004

(54) **METHOD FOR PREPARING SUBSTITUTED [1,4]DIAZEPINO[6,7,1-*HI*]INDOL-4-ONES**

(75) Inventor: Patrick Bernardelli, Fontenay Aux Roses (FR)

(73) Assignee: Warner-Lambert LLC, Morris Plains, NJ (US)

( * ) Notice: Subject to any disclaimer, the term of this patent is extended or adjusted under 35 U.S.C. 154(b) by 0 days.

(21) Appl. No.: 10/019,191

(22) PCT Filed: Jun. 29, 2000

(86) PCT No.: PCT/FR00/01839

§ 371 (c)(1),
(2), (4) Date: Apr. 3, 2002

(87) PCT Pub. No.: WO01/02403

PCT Pub. Date: Jan. 11, 2001

(30) Foreign Application Priority Data

Jul. 2, 1999 (FR) .............................. 99 08537

(51) Int. Cl.⁷ ............................................ C07D 487/06
(52) U.S. Cl. ...................................................... 540/496
(58) Field of Search ......................................... 540/496

(56) References Cited

U.S. PATENT DOCUMENTS

| | | | |
|---|---|---|---|
| 5,256,801 A | 10/1993 | Carver et al. ................ | 549/510 |
| 5,342,971 A | 8/1994 | Herlt et al. .................. | 549/390 |

FOREIGN PATENT DOCUMENTS

| | | |
|---|---|---|
| EP | 0 617 016 A1 | 9/1994 |
| WO | WO 94/14790 | 7/1994 |
| WO | WO 98/49169 | 11/1998 |

OTHER PUBLICATIONS

Quantitative Aspects of Lewis Acidity, Satchell, D.P.N., and Satchell, R.S.; Quarterly Reviews (The Chemical Society London), 1971; 25:171–199.

Lanthanide triflates as unique Lewis acids, Xie, W.; Jin, Y.; Wang, P.G.; Chemtech, 1999; 29:23–29.

Marshman, R.W., Rare earth triflates in organic synthesis, Aldrichimica Acta, 1995; 28:77–84.

Primary Examiner—Bruck Kifle
(74) Attorney, Agent, or Firm—Peter C. Richardson; Gregg C. Benson; Robert T. Ronau

(57) ABSTRACT

Method for the preparation of enantiomerically pure diazepino-indolone of formula

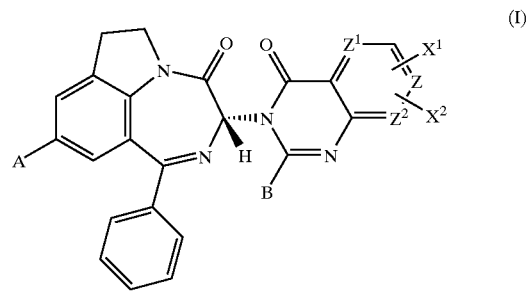

which comprises the intramolecular cyclization of a product of formula

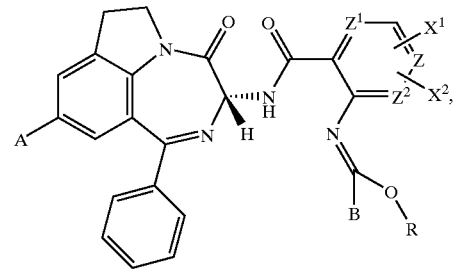

where A, B, $X^1$, $X^2$, Z, $Z^1$, $Z^2$ and R are as defined in the description, in the presence of a weak Lewis acid catalyst.

4 Claims, No Drawings

METHOD FOR PREPARING SUBSTITUTED [1,4]DIAZEPINO[6,7,1-*HI*]INDOL-4-ONES

FIELD OF THE INVENTION

The present invention relates to a novel method for the preparation of chiral [1,4]diazepino[6,7,1-*hi*]-indol-4-ones of use in the preparation of medicaments which make possible the treatment of ailments involving therapy by an inhibitor of phosphodiesterases 4 (PDE4). These medicaments are of use in particular as antiinflammatories, antiallergics, bronchodilators or antiasthmatics.

The international patent application published under No. WO 98/49169, the contents of which are incorporated in the present application by reference, discloses diazepino-indolones, which are compounds active as inhibitors of PDE4 enzymes, of formula

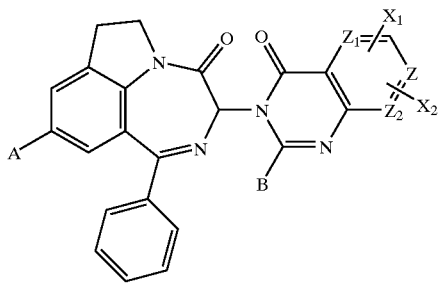

in which:

A is hydrogen, lower alkyl, lower alkoxy, nitro or amino;
B is hydrogen or optionally functionalized lower alkyl;
$X_1$ and $X_2$, which are alike or different, can be hydrogen, halogen, lower alkyl, lower alkoxy or alternatively —$CH_2OH$ or —$CO_2H$, which are optionally substituted;
Z is CH, then $Z_1$ and $Z_2$ are both CH or N; or Z is N, then $Z_1$ and $Z_2$ are CH.

In this Application WO 98/49169, the preferred diazepino-indolones of formula (I) are those in which the 3 carbon of the [1,4]diazepino[6,7,1-*hi*]indol-4-one nucleus has the S configuration.

These compounds were obtained in Patent Application WO 98/49169 as racemic compounds and could only be separated by chiral phase chromatography or else by the formation of salts with an enantiomerically pure amine. The synthetic process disclosed in Patent Application WO 98/49169 can exhibit disadvantages, including, on occasions, low yields and the need for a resolution stage.

SUMMARY OF THE INVENTION

In point of fact, an improved process has now been found for the preparation of these same products directly in the form of pure enantiomers, which process is efficient and economic and forms the subject-matter of the present invention. Consequently, the present process avoids the disadvantages of the known processes and it can be adapted to a larger scale.

The invention relates to an improved process for the preparation of chiral substituted [1,4]diazepino[6,7,1-*hi*] indol-4-ones of formula (I)

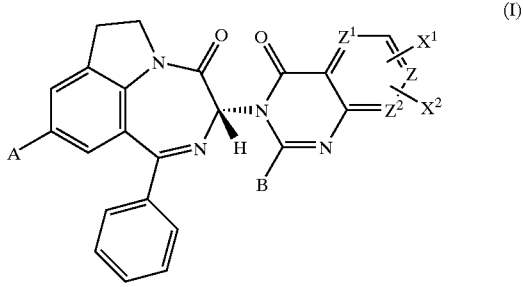

in which, in particular:

A is hydrogen, lower alkyl, lower alkoxy, nitro or amino;
B is hydrogen or lower alkyl;
Z is CH, then $Z^1$ and $Z^2$ are together CH or N; or Z is N, then $Z^1$ and $Z^2$ are CH;
$X^1$ and $X^2$, which are alike or different, can be hydrogen, halogen, lower alkyl, lower alkoxy or alternatively —$CH_2OH$ or —$CO_2H$, which are optionally substituted.

DETAILED DESCRIPTION OF THE INVENTION

The invention is targeted at a process for the preparation of the enantiomers of the diazepino-indolones (I) of formula

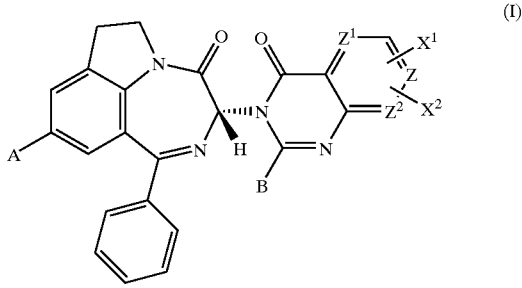

in which:

A is hydrogen, lower alkyl, hydroxyl, lower alkoxy, nitro, cyano or $NR^1R^2$; $R^1$ and $R_2$ are independently hydrogen or lower alkyl or form, together with the nitrogen atom to which they are bonded, a ring having 4 or 5 carbon atoms;
B is hydrogen or lower alkyl;
Z is CH, then $Z^1$ and $Z^2$ are together CH or N; or Z is N, then $Z^1$ and $Z^2$ are CH;
$X^1$ and $X^2$ are independently hydrogen, $C_1$–$C_4$ alkyl, —$(CH_2)_j$—$OR^3$, halogen, cyano, —O—($C_1$–$C_6$ alkyl), —$C(=O)R^4$, —$C(=O)OR^5$, —$C(=O)NR^6R^7$, or

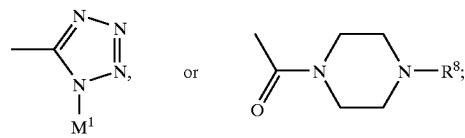

$R^3$, $R^4$ and $R^5$ are independently hydrogen, $C_1$–$C_6$ alkyl, benzyl, phenethyl or —$Q^1$—$Q^2$;
$R^6$ is hydrogen or $C_1$–$C_4$ alkyl;
$R^7$ is hydrogen, $C_1$–$C_4$ alkyl, —$CHR^A$—$C(=O)OM^2$ or —$Q^3$—$Q^4$;

$R^8$ is hydrogen, $C_1$–$C_4$ alkyl or —$Q^5$—$Q^6$;
$R^A$ is a natural α-amino acid residue, the carbon atom to which it bonded being able to have either the S configuration or the R configuration;
$Q^1$ is —$(CH_2)_k$—$(CHOH)_m$—$(CH_2)_p$—;
$Q^2$ is hydroxyl, —O—($C_1$–$C_6$ alkyl), —OC(=O)—($C_1$–$C_6$ alkyl) or 4-morpholinyl;
$Q^3$ and $Q^5$ are independently a bond, —$CH_2$—, —$(CH_2)_2$— or —$(CH_2)_3$—;
$Q^4$ is —$NM^3M^4$ or 4-morpholinyl;
$Q^6$ is —$M^5$ or —$OM^6$;
$M^1$, $M^2$, $M^3$, $M^4$, $M^5$ and $M^6$ are independently hydrogen or $C_1$–$C_4$ alkyl;
j is 1, 2 or 3; k is 1, 2 or 3;
m is 0, 1, 2, 3 or 4; p is 0, 1, 2 or 3, with the proviso that, if m>0, then p>0;
their isomers, their racemic forms, as well as their salts, solvates, esters, amides and prodrugs which are pharmaceutically acceptable.

In what precedes and in what follows:
the term "halogen" is understood to mean fluorine, chlorine, bromine or iodine;
the term "lower alkyl" or "$C_1$–$C_4$ alkyl" is understood to mean a linear or branched radical comprising from 1 to 4 carbon atoms or alternatively the cyclopropylmethyl radical;
the term "lower alkoxy" is understood to mean a radical of formula —O-Alk, where Alk is lower alkyl;
the term "$C_1$–$C_6$ alkyl" is understood to mean a linear or branched radical comprising from 1 to 6 carbon atoms or alternatively the cyclopropylmethyl radical.

The process of the present invention makes it possible to obtain the chiral [1,4]diazepino[6,7,1-*hi*]indol-4-ones (I) directly, in the form of pure enantiomers, from optically active 3-aminobenzodiazepines (II) in a stage represented in Scheme 1, Scheme 1:

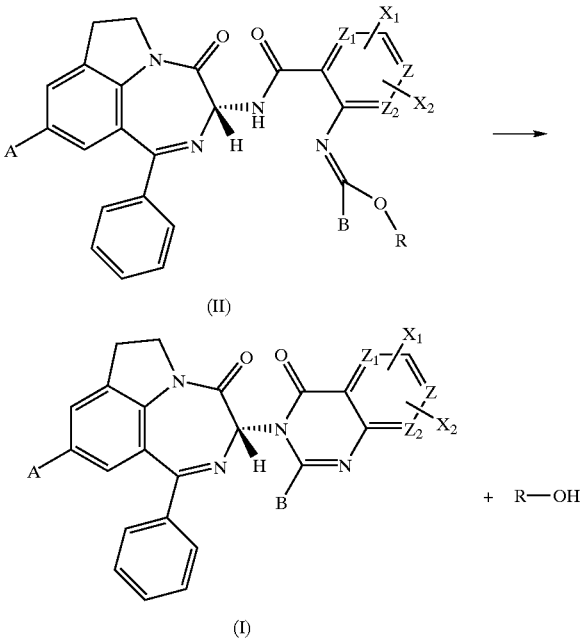

where A, Z, $Z^1$, $Z^2$, B, $X^1$ and $X^2$ have the meanings defined above for (I);
R is a lower alkyl radical, preferably the methyl radical.

During this reaction, an intermediate (II) is cyclized, preferably at normal temperature or below 0° C., in the presence of a Lewis acid, such as scandium trifluoromethanesulphonate, to give the product (I).

The intermediate (II) is dissolved in a solvent and a catalytic amount of Lewis acid, preferably scandium trifluoromethanesulphonate, is added at normal temperature. The product (I) is obtained, the optical purity of which is confirmed by analytical HPLC.

More generally, the Lewis acids of use in the process of the present invention are described in particular in the following publications: i) *Advanced Organic Chemistry*, Third Edition, by Jerry March (John Wiley & Sons, New York, 1985); ii) "Friedel-Crafts Reactions", Olah, G. and Meidar, D.; *Kirk-Othmer Encyclopedia of Chemical Technology*, Third Edition, 11, 269–300 (John Wiley & Sons, New York, 1978), iii) "Quantitative Aspects of Lewis Acidity", Satchell, D. P. N. and Satchell, R. S.; *Quarterly Reviews* (The Chemical Society, London), 1971, 25: 171–199, iv) "Lanthanide triflates as unique Lewis acids", Xie, W., Jin, Y. and Wang, P. G.; *CHEMTECH*, 1999, 29, 23–29, and v) Marshman, R. W., "Rare earth triflates in organic synthesis", *Aldrichimica Acta*, 1995, 28, 77–84.

Strong Lewis acids (such as aluminium chloride, ferric chloride and equivalents) do not seem, in the present invention, as effective catalysts as weak Lewis acids.

Examples of Lewis acids of use in the present invention are compounds or complexes of formula:

$$[LX_xY_y]$$

having a vacant orbital,
where L is a metal, boron, silicon or antimony,
X and Y are neutral or anionic, nonmetallic ligands, atoms or radicals,
x and y are each zero or an integer.

Typical values of L comprise boron, aluminium, silicon, scandium, titanium, gallium, indium, yttrium, zirconium, silver, tin, antimony, lanthanum and lanthanides, mercury, thallium, manganese, iron, cobalt, nickel, copper, zinc, calcium and magnesium or another transition metal. Preferred values of L comprise boron, silicon, aluminium, scandium, lanthanides, titanium, gallium, silver, tin, iron, zinc and magnesium.

Typical values of X and Y are chosen from halides, oxygen, oxygen-comprising ligands, organic radicals and organic anions.

The oxygen-comprising ligands comprise, for example, oxygen or alkoxy, phenoxy, carboxylate, β-ketocarboxylate, sulphate, sulphonate, phosphate, phosphonate and equivalent radicals.

The organic radicals comprise, for example, alkyl, substituted alkyl, cycloalkyl, substituted cycloalkyl, phenyl, substituted phenyl, phenylalkyl and (substituted phenyl) alkyl radicals.

The organic anions comprise cyclopentadienyl and substituted cyclopentadienyl anions.

The Lewis acids preferably comprise at least one oxygen-comprising ligand, for example an alkoxy radical or a sulphonate radical. The preferred weak Lewis acids are boron, aluminium, silicon, scandium, lanthanide, titanium, gallium, silver, tin, iron, zinc or magnesium complexes comprising at least one oxygen-comprising ligand. Specific examples of weak Lewis acids of use in the present invention are scandium trifluoromethanesulphonate, aluminium trifluoromethane-sulphonate, as well as ytterbium or other lanthanide, silicon, magnesium, tin(II), copper(II), zinc or silver trifluoromethanesulphonates; dimethoxydicyclopenta-dienyltitanium(IV) or dicyclopentadienyltitanium(IV) bis(trifluoromethanesulphonate); iron(III), aluminium or zinc acetylacetonate; zinc diacetate; dimethoxymagnesium; triisopropoxyaluminium, tetrabutoxytitanium(IV), tetraisopropoxytitanium(IV), trimethylboron, triethylaluminium, diethylzinc, triisobutylaluminium, tetrabutyltin(IV), triphenyl-boron, triphenylantimony; or halides, in particular zinc, tin(II), antimony(III), antimony(V), titanium(III), titanium(IV), scandium, indium, gallium and mercury(II) chlorides or, preferably, bromides.

The cyclization reaction is carried out in an inert solvent, that is to say a solvent or mixture of solvents which does not react with the reactants or the reaction products and which does not react in an unfavourable way with the Lewis acid catalyst. The solvent is aprotic and preferably not very polar. Representative solvents are: aromatic hydrocarbons, such as benzene, toluene, nitrobenzene or chlorobenzene; aliphatic hydrocarbons, such as pentane, hexane or heptane; dialkyl ethers, such as ethyl or isopropyl ether; chlorinated hydrocarbons, such as dichloromethane, trichloromethane, tetrachloromethane or dichloroethylene; 1,1,1-trimethoxyalkanes, such as trimethyl orthoacetate; cyclic ethers, such as tetrahydrofuran or dioxane; and their mixtures. It is not necessary for the reactants or the catalyst to be completely dissolved in the solvent used.

The amount of Lewis acid used generally represents from 1 to 10 mol equivalent % with respect to the starting material (II). In this cyclization reaction, the minimum amount of Lewis acid relative to the product of formula (II) depends on the activity of the Lewis acid under consideration, on the temperature reaction and on its maximum allotted duration; it is determined by routine experiments. The Lewis acid can advantageously be easily recycled at the end of the reaction.

The Lewis acid catalyst is preferably soluble in the solvent used.

A dehydrating agent, such as anhydrous magnesium sulphate or a molecular sieve, can optionally be introduced into the cyclization reaction mixture.

The cyclization reaction is carried out at a temperature of between approximately 0° C. and 40° C. and preferably between approximately 25° C. and 40° C. It is advisable not to exceed 40° C. in order not to epimerize the stereogenic centre.

The duration of the reaction is generally between 6 and 48 h. Its progress can be monitored by analytical HPLC or TLC; the reaction is thus stopped after the starting material has disappeared.

When A is a primary amine group in the final product, the process comprises an additional stage where a product (I), in which A is —NO$_2$, is reduced to a product (I), in which A is —NH$_2$, by a chemical or catalytic reduction which respects the asymmetric carbon. This stage consists in specifically reducing a compound (I), in which A is nitro, which reduction is carried out by appropriate reducing systems: these are, inter alia, zinc in acid medium, titanium chloride in acid medium or else tin chloride in ethanolic medium; this stage is represented in the experimental part below by the synthesis of the products 7, 13 and 18.

These reductions are carried out under cold conditions but the preferred reduction is carried out in methanol, with ruthenium-on-charcoal as catalyst, at a temperature not exceeding 80° C. and under a hydrogen pressure of 400 to 800 kPa. The hydrogenation time should be less than 2 h and preferably 1.5 h.

The intermediate (II) can be prepared according to the process presented in Scheme 2, where A, Z, $Z^1$, $Z^2$, $X^1$ and $X^2$ have the meanings defined for (I) and PG is a protecting group.

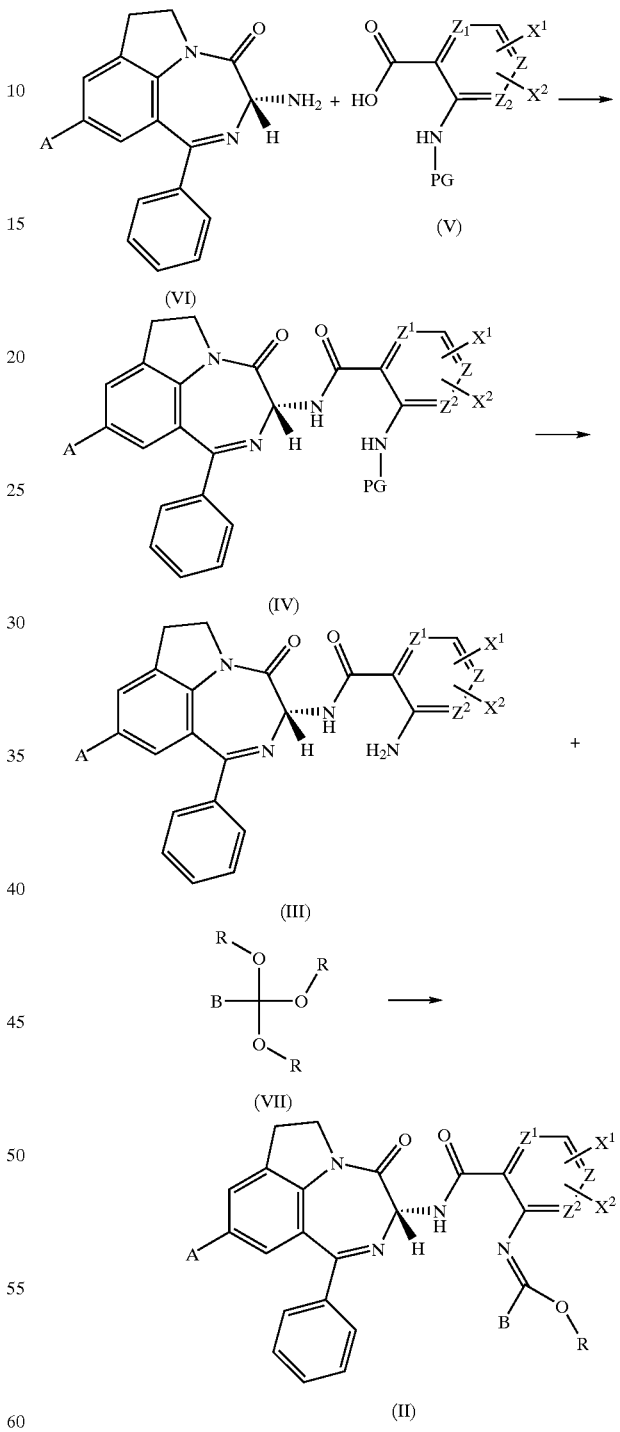

The first stage consists of the condensation of an optically active aminobenzodiazepine (VI) with a suitably substituted anthranilic acid (V) protected on the amine functional group, in order to obtain an intermediate (IV).

The intermediate (IV) is subsequently deprotected to give the intermediate (III) with a free amine functional group.

The intermediate (III), reacted with an appropriate ortho ester (or 1,1,1-trialkoxyalkane) (VII) under mild conditions, in order not to epimerize the asymmetric carbon of the benzodiazepine, gives an intermediate (II).

In some cases, an anthranilic acid (V') which is unprotected on the amine functional group can be condensed directly with the aminobenzodiazepine (VI), which directly provides the intermediate compound (III) (Process B).

More specifically, Process A, as presented in Scheme 2, comprises the preparation of the intermediates (IV) by reaction of an amino intermediate (VI) with an intermediate (V) prepared from a 2-anthranilic acid. It consists, with a protected 2-anthranilic acid (V), in carrying out, in a first stage, the N-acylation of the amine (VI). The operation is carried out in an anhydrous organic solvent, such as a chlorinated hydrocarbon, for example dichloromethane or trichloromethane, a linear or cyclic ether, such as 1,2-dimethoxyethane, tetrahydrofuran or dioxane, a polar aprotic solvent, such as pyridine, dimethyl sulphoxide or N,N-dimethylformamide (DMF), or any other suitable solvent and their mixtures. The reaction is advantageously carried out in the presence of a coupling agent and optionally of an organic base.

Thus, use is made, as coupling agent, of:

an O-[(ethoxycarbonyl)cyanomethylamino]-N,N,N',N'-tetramethyluronium tetrafluoroborate/N,N-diisopropylethylamine combination, or an isobutyl chloroformate/N-methylmorpholine combination, or preferably, a combination of hydroxybenzotriazole (HOBT) and of a carbodiimide, such as N,N'-dicyclohexylcarbodiimide (DCC), which is the preferred reagent, N,N'-diisopropylcarbodiimide or carbonyldiimidazole, in a neutral anhydrous solvent, such as dichloromethane or DMF, at 0° C.

In this first stage of Process A, the t-butoxycarbonylamino acid (V) is used in the isolated form.

The second stage consists in deprotecting the amine functional group of the intermediate (IV), in order to obtain the primary amine (III). With this aim, the intermediate (IV) can be dissolved in an acid, such as trifluoroacetic acid, which is the preferred process, and left to react for a time which depends on the nature of the protecting group employed. In the case of the preferred protecting group PG, which is the t-butoxycarbonyl group, hereinafter "t-BOC", the products are left in contact for half an hour and the mixture is evaporated. The product is taken up in dichloromethane and neutralized with a 5% aqueous NaHCO$_3$ solution.

The intermediate (III) is obtained.

In the experimental part which illustrates the invention, Examples 1, 2, 4 and 5 are representative of Process A.

The intermediate (III) can also be obtained, with a possibly lower yield, by direct coupling of an anthranilic acid which is unprotected on the amine functional group (V') with the starting enantiomeric amine (VI) by Process B.

In this case, the coupling agent can also be the DCC/HOBT combination. Use may be made, for this stage, of other acids, such as formic acid, dichloroacetic acid or any other organic or inorganic acid, mixed or not with a solvent in various proportions, at a concentration and at a temperature such that there is no hydrolysis of the benzodiazepine nucleus.

In the experimental part, Example 3 is representative of Process B.

Process B:

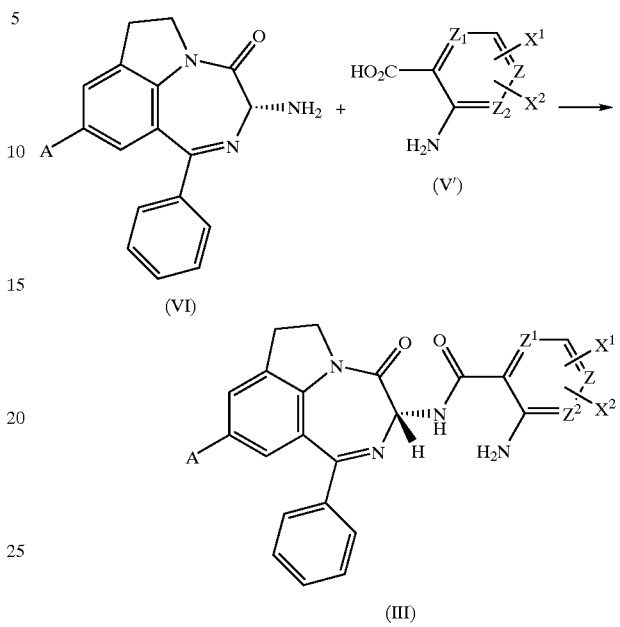

Starting from the intermediate (III), the following stages are common to both processes.

In the third stage, a solution of the intermediate (III) is stirred with an ortho ester (VII), preferably a methyl ortho ester, in order to obtain the intermediate (II), which is not purified but is employed as is in the following stage. During this third stage, it is advisable to remain at low temperature and in particular not to exceed 40° C., failing which (III) and (II) would epimerize to give a racemic mixture. The duration of the coupling can reach 24 h but it is sometimes much faster. It is possible, by vacuum distillation, to remove the methanol which has formed during the reaction; the reaction is thus complete.

The protected and substituted anthranilic acids (V) are described in the literature; if not, they are prepared in a way analogous to the preparation of 2-(t-butoxycarbonylamino) benzoic acid 2, which preparation is described in the experimental part below.

EXPERIMENTAL PART

The following examples illustrate, without, however, limiting it, the implementation of the process according to the invention and the products obtained. The process disclosed in the present application illustrates the preparation of a product of formula (I) which is an S enantiomer; with this teaching, the preparation of the corresponding R antipode, from the appropriate chiral intermediate, according to the process of the invention is within the scope of a person skilled in the art.

The purity, the identity and the physicochemical characteristics of the products and of the essential intermediates prepared are determined; thus:

the purity is confirmed by thin layer chromatography (T.L.C.) operations using silica gel (Merck 60-F254) and the Rf observed is reported for the elution solvent used, which is usually identical with that used for the chromatographic analysis of the compounds. These solvents are identified by the following abbreviations:

D/M1: dichloromethane/methanol, 99/1 (v/v),
D/M2: dichloromethane/methanol, 98/2 (v/v),
D/M5: dichloromethane/methanol, 95/5 (v/v),
D/MN5: dichloromethane/10% ammoniacal methanol, 95/5 (v/v),
D/MN20: dichloromethane/10% ammoniacal methanol, 80/20 (v/v), the identity of the products obtained with the proposed structures is confirmed by their proton nuclear magnetic resonance spectrum and by their infrared spectrography.

The $^1$H N.M.R. spectra are run at 400 MHz on a device of Brüker trademark, the compounds being dissolved in deuterochloroform with tetramethylsilane as internal reference. The nature of the signals, their chemical shifts in ppm and the number of protons which they represent are noted.

The infrared spectra are recorded as a potassium bromide disc on a Shimadzu IR-435 spectrometer.

The optical purity of the various enantiomers is confirmed on an analytical high pressure liquid chromatography system of Merck type by injection on a 250×4.6 mm Pirkle D-phenylglycine chiral column, 5 μm particles, thermostatically controlled at 35° C., eluent: hexane/ethanol 50/50 (v/v), flow rate 1 ml/min. The result, calculated in the form of enantiomeric excess (ee), is given by the formula:

$$ee = \frac{\text{mass of } (S) \text{ enantiomer} - \text{mass of } (R) \text{ enantiomer}}{\text{mass of } (S) \text{ enantiomer} + \text{mass of } (R) \text{ enantiomer}}$$

the physicochemical characteristics, recorded in so far as there is sufficient product available, are the uncorrected melting point, determined by the capillary tube method, and the optical rotation, determined at ambient temperature in the region of 20° C. on a Polartronic device in a cell with a length of 10 cm.

As regards the experimental description:

the term "concentrating or removing the solvents" is understood to mean, optionally after they have been dried over an appropriate dehydrating agent, such as $Na_2SO_4$ or $MgSO_4$, distilling under a vacuum of 25 to 50 mm Hg (3.3 to 6.7 kPa) and with moderate heating on a water bath (at a temperature of less than 30° C.);

the term "flash chromatography on a silica column" is understood to mean the use of a method adapted from that of Still et al. (1978), J. Org. Chem., 43, 2923, the purity of the elution fractions being confirmed before they are combined and evaporated under the conditions defined above.

EXAMPLE 1

(3S)-3-(2-Methyl-4-oxo-4H-quinazolin-3-yl)-9-amino-1-phenyl-6,7-dihydro-3H-[1,4]diazepino[6,7,1-hi]indol-4-one. (7)

[(I); A=$NH_2$, Z=CH, $Z^1$=CH, $Z^2$=CH, B=$CH_3$, $X^1$=H, $X^2$=H](Process A)

1) Synthesis of the Intermediate (II)

Intermediate 1: (3R)-3-Amino-9-nitro-1-phenyl-6,7-dihydro-3H-[1,4]diazepino[6,7,1-hi]indol-4-one. [(VI); A=$NO_2$].

51.0 ml of concentrated sulphuric acid (d=1.83) are introduced into a 100 ml reactor and, with stirring, 16.0 g (57.7 mmol) of (3R)-3-amino-1-phenyl-6,7-dihydro-3H-[1,4]diazepino[6,7,1-hi]indol-4-one, prepared as disclosed for the intermediate 1.b of Patent FR94/12282, are added. During the exothermic introduction, the temperature reaches 70° C.; the brown solution obtained is cooled to 5–10° C. 6.93 g (68.5 mmol) of pure potassium nitrate, dissolved in 17.0 ml of sulphuric acid (d=1.83), are then rapidly introduced. The temperature rises to 40° C. and then the reaction mixture is maintained at 20° C. with stirring for 40 min. The brown solution is precipitated from 600 ml of a mixture of water and ice. The mixture is basified with a concentrated aqueous ammonium solution and then extracted with 3 times 150 ml of dichloromethane. The organic phases are washed with water and dehydrated and the solvents are subsequently removed by distillation. A light brown foamy residue is obtained (17.5 g), which residue is purified by silica flash chromatography. Elution with dichloromethane progressively enriched in methanol makes it possible to obtain 12.0 g of purified product 1.

Yd=75% M.p.=177–178° C.; $[\alpha]_D$(c=0.4, $CH_2Cl_2$)=+66.8° C.

Intermediate 2: 2-(t-Butoxycarbonylamino)benzoic Acid.

[(V); Z=CH, $Z^1$=CH, $Z^2$=CH, $X^1$=H, $X^2$=H]

22 g (160 mmol) of anthranilic acid are dissolved with stirring in 300 ml of methanol comprising 10% of triethylamine in a reactor protected from moisture. 38.68 g of di-t-butyl dicarbonate are added and the mixture is heated at reflux for 4 h. The mixture is evaporated, the residue is taken up in ethyl acetate and the organic solution is washed with a normal $KHSO_4$ solution and washed with water. The solution is evaporated, the residue is taken up in dichloromethane and the insoluble material is filtered off: 20 g of the expected product (V). The residue is chromatographed on silica in dichloromethane enriched in ethyl acetate. A further 9 g of the expected product 2 are obtained. Overall Yd: 76%.

Intermediate 3: [2-((3R)-9-Nitro-4-oxo-1-phenyl-3,4,6,7-tetrahydro[1,4]diazepino[6,7,1-hi]indol-3-ylcarbamoyl)phenyl]carbamic Acid t-Butyl Ester.

[(IV); A=$NO_2$, Z=CH, $Z^1$=CH, $Z^2$=CH, $X^1$=H, $X^2$=H, PG=t-BOC]

7 g (32 mmol) of 2 are dissolved with stirring in 250 ml of dry dichloromethane in a reactor protected from moisture. The mixture is cooled to 0° C. and 10 g (32 mmol) of 1 in 30 ml of dichloromethane are added. 4.32 g (32 mmol) of hydroxybenzotriazole (HOBT) and 6.6 g (32 mmol) of dicyclohexylcarbodiimide (DCC) are added. After stirring for 4 h at 0° C., the insoluble material is filtered off and the filtrate is successively extracted with a 0.1N $HKSO_4$ solution, a saturated $NaHCO_3$ solution and, finally, with water. The solvent is evaporated under vacuum at 0° C. and the residue is purified by flash chromatography on a silica column, elution being carried out with the solvent dichloromethane/5% ethyl acetate. 10 g of a white crystalline solid are obtained.

Yd=60%. T.L.C. (D/M1): Rf=0.43. H.P.L.C. (Pirkle/D-phenylglycine column, eluent hexane/ethanol 50/50, T=35° C., flow rate: 1 ml/min, UV: 254 nm): ee=93.2% $^1$H N.M.R., δ (ppm): 1.5 (s, 9H), 3.2–3.6 (m, 2H), 4.05–4.25 (m, 2H), 4.75 (m, 1H), 5.65 (d, 1H), 7.08 (t, 1H), 7.4–7.6 (m, 5H), 7.80 (d, 1H), 7.88 (d, 1H), 8.22 (d, 2H), 8.3 (s, 1H), 8.40–8.45 (d, 1H), 10.1 (s, 1H).

Intermediate 4: 2-Amino-N-((3R)-9-nitro-4-oxo-1-phenyl-3,4,6,7-tetrahydro[1,4]diazepino[6,7,1-hi]indol-3-yl)benzamide.

[(III): A=$NO_2$, Z=CH, $Z^1$=CH, $Z^2$=CH, $X^1$=H, $X^2$=H]

10 g (19 mmol) of 3 are introduced into 500 ml of dichloromethane in a 50 ml reactor protected from moisture and under a nitrogen atmosphere and then, at 0° C., 75 g (665 mmol) of trifluoroacetic acid are introduced. The mixture is stirred for 1 h at 0° C. and is evaporated at 0° C.

under vacuum. The residue is taken up in ethyl acetate and the organic solution is washed with an NaHCO$_3$ solution and then with an NaCl solution and evaporated at 0° C. Crude product: 8.4 g.

The product is employed crude in the following stage.

T.L.C. (D/M1): Rf=0.29. ee: 95.9%. $^1$H N.M.R., δ (ppm): 3.25 (s, 2H, exchangeable), 3.1–3.5 (m, 2H), 3.9–4.12 (m, 1H), 4.4–4.6 (m, 1H), 5,12 (d, 1H), 6.35 (s, 1H, exchangeable), 6.45–6.6 (t, 1H), 6.65 (d, 1H), 7.12 (t, 1H), 7.35–7.6 (m, 4H), 7.6–7.9 (m, 1H), 7.9–8.1 (m, 1H), 8.38 (s, 1H), 9.25 (m, 1H).

Intermediate 5: N-[2-((3R)-9-Nitro-4-oxo-1-phenyl-3,4,6,7-tetrahydro[1,4]diazepino[6,7,1-*hi*]indol-3-ylcarbamoyl)phenyl]acetimidic Acid Methyl Ester.

[(II); A=NO$_2$, Z=CH, Z$^1$=CH, Z$^2$=CH, B=CH$_3$, X$^1$=H, X$^2$=H, R=CH$_3$]

500 ml of trimethyl orthoacetate and 8.4 g of 4 are introduced into a reactor protected from moisture and under a nitrogen atmosphere. The stirred reactor is placed under a vacuum of 0.1 kPa and is heated at 40° C. for 6 h. The mixture is evaporated under vacuum and NMR confirms the existence of the new product 5: 10 g of crude reaction product.

HPLC: ee>95%. TLC (D/M2): Rf=0.87. $^1$H N.M.R., δ (ppm): 1.95 (s, 3H), 3.1–3.6 (m, 2H), 4.0 (s, 3H), 3.95–4.22 (m, 1H), 4.65–4.8 (m, 1H), 5.7 (d, 1H), 6.85 (d, 1H), 7.15–7.30 (m, 1H), 7.35–7.55 (m, 6H), 8.15–8.25 (m, 2H), 8.3 (s, broad, 1H), 9.65 (d, 1H).

2) (3S)-3-(2-Methyl-4-oxo-4H-quinazolin-3-yl)-9-amino-1-phenyl-6,7-dihydro-3H-[1,4]diazepino[6,7,1-*hi*]indol-4-one. (7)

Product 6: (3S)-3-(2-Methyl-4-oxo-4H-quinazolin-3-yl)-9-nitro-1-phenyl-6,7-dihydro-3H-[1,4]diazepino[6,7,1-*hi*]indol-4-one.

[(I): A=NO$_2$, Z=CH, Z$^1$=CH, Z$^2$=CH, X$^1$=H, X$^2$=H]

500 ml of dichloromethane and 10 g of 5 are introduced into a reactor protected from moisture and under a nitrogen atmosphere. 0.2 g of scandium trifluoromethanesulphonate is added and the mixture is left stirring at ambiant temperature (18° C.) for 18 h. Washing is carried out with an NaHCO$_3$ solution and the organic phase is dried and evaporated. The residue is purified by silica chromatography, the elution being carried out with a gradient of methanol in dichloromethane. 88% of a product 6 are obtained.

HPLC: ee=94%. $^1$H N.M.R., δ (ppm): 2.70 (s, 3H), 3.2–3.6 (m, 2H), 4.0–4.25 (q, 1H) 4.7–4.9 (m, 1H), 7.28 (s, 1H), 7.35–7.65 (m, 6H), 7.65–7.85 (m, 2H), 8.15–8.28 (m, 2H), 8.30–8.35 (m, 1H).

Product 7: [(I); A=NH$_2$, Z=CH, Z$^1$=CH, Z$^2$=CH, X$^1$=H, X$^2$=H]

1.5 g of the product 6 obtained in the preceding stage are hydrogenated at 80° C. in 150 ml of methanol, in the presence of 1.3 g of 5% ruthenium-on-charcoal, under a pressure of 800 kPa. After cooling, filtering and rinsing the catalyst with methanol, the solvent is evaporated. The product is chromatographed in a gradient of dichloromethane enriched in methanol. Yd=55%. TLC (DM2):

Rf=0.25. HPLC: ee=94%. $^1$H N.M.R., δ (ppm): 2.8 (s, 3H), 3 (m, 1H), 3.2 (m, 1H), 3.85 (q, 1H) 4.5 (q, 1H), 6.4 (s, 1H), 6.8 (s, 1H), 7.1 (s, 1H), 7.4–7.6 (m, 7H), 7.7 (m, 2H), 7.9 (m, 1H). 8.15 (d, 1H). I.R.: 3300, 1660, 1580, 1480, 1380, 1300, 1240, 1100, 880, 780, 700 cm$^{-1}$.

EXAMPLE 2

2-Methyl-3-((3S)-9-amino-4-oxo-1-phenyl-3,4,6,7-tetrahydro[1,4]diazepino[6,7,1-*hi*]indol-3-yl)-4-oxo-3,4-dihydroquinazoline-7-carboxylic Acid Methyl Ester. (13)

[(I); A=NH$_2$, Z=CH, Z$^1$=CH, Z$^2$=CH, B=CH$_3$, X$^1$=H, X$^2$=CO$_2$CH$_3$ in 7.]

This product is prepared from the same nitrated amine 1 as for Example 1, and from the monomethyl ester of protected 2-aminoterephthalic acid, itself prepared in two stages from 2-aminoterephthalic acid.

1) Synthesis of the Intermediate (II)

Intermediate 9: 3-(t-Butoxycarbonylamino)-N-((3R)-9-nitro-4-oxo-1-phenyl-3,4,6,7-tetrahydro-[1,4]diazepino[6,7,1-*hi*]indol-3-yl)terephthalamic Methyl Ester.

[(IV); A=NO$_2$, Z=CH, Z$^1$=CH, Z$^2$=CH, X$^1$=H, X$^2$=CO$_2$CH$_3$, PG=t-BOC]

7 g (32 mmol) of 2-(t-butoxycarbonylamino)terephthalic acid 4-methyl ester are dissolved with stirring in 250 ml of dry dichloromethane in a reactor protected from moisture. The mixture is cooled to 0° C. and 10 g (32 mmol) of 1 in 30 ml of dichloromethane are added. 4.32 g (32 mmol) of HOBT and 6.6 g (32 mmol) of DCC are added. After stirring for 4 h at 0° C., the insoluble material is filtered off and the filtrate is extracted successively with a 0.1N HKSO$_4$ solution, a saturated NaHCO$_3$ solution and, finally, with water. The solvent is evaporated under vacuum at 0° C. and the residue is purified by flash chromatography on a silica column, elution being carried out with the solvent dichloromethane/5% ethyl acetate. 10 g of 9 are obtained. Yd=60%.

$^1$H N.M.R., δ (ppm): 1.42 (s, 9H), 3.12–3.6 (m, 2H), 3.95–4.2 (m, 1H), 4.05 (s, 3H), 4.52 (m, 1H), 5.62 (d, 1H), 7.4–7.65 (m, 4H), 7.65–7.72 (m, 1H), 7.72–8.1 (m, 1H), 8.15 (d, 1H), 8.42 (s, 1H), 8.8.82 (d, 1H), 10.16 (d, 1H), 10.26 (s, 1H), 10.88 (s, 1H). H.P.L.C. (Pirkle column, D-phenylglycine, eluent hexane/ethanol 50/50, T=35° C., flow rate 1 ml/min, UV 254 nm): ee=93.2%.

Intermediate 10: 3-Amino-N-((3R)-9-nitro-4-oxo-1-phenyl-3,4,6,7-tetrahydro[1,4]diazepino[6,7,1-*hi*]indol-3-yl)terephthalamic Acid Methyl Ester.

[(III); A=NO$_2$, Z=CH, Z$^1$=CH, Z$^2$=CH, X$^1$=H, X$^2$=CO$_2$CH$_3$ at the para position]

27 g of 9 are dissolved in 1.4 l of dichloromethane and 140 ml of trifluoroacetic acid are slowly added. The reaction mixture is left stirring for 1 h at normal temperature and is evaporated under vacuum at a temperature of less than 25° C. The residue is taken up in 1 l of dichloromethane and washed with a 5% solution of NaHCO$_3$ in water and then with water saturated with NaCl. The organic phase is dried over sulphate and is evaporated at a temperature of less than 25° C. After chromatography on silica in dichloromethane enriched in methanol, 21.4 g (95%) of an oil 10 are obtained.

$^1$H N.M.R., δ (ppm): 3.35 (s, 2H, exchangeable), 3.1–3.5 (m, 2H), 3.9–4.15 (m, 1H), 3.95 (s, 3H), 4.55–4.65 (m, 1H), 5.23 (s, 1H), 5.60 (d, 1H), 7.30–7.50 (m, 6H), 7.70–7.80 (m, 1H), 8.05–8.35 (m, 3H).

Intermediate 11: 3-(1-Methoxyethylidenamino)-N-((3R)-9-nitro-4-oxo-1-phenyl-3,4,6,7-tetrahydro-[1,4]diazepino[6,7,1-*hi*]indol-3-yl)terephthalamic Acid Methyl Ester.

[(II); A=NO$_2$, Z=CH, Z$^1$=CH, Z$^2$=CH, B=CH$_3$, X$^1$=H, X$^2$=para-CO$_2$CH$_3$]

20 g of 10 are dissolved in 750 ml of trimethyl orthoacetate. 840 mg of scandium trifluoromethanesulphonate are added and the mixture is stirred at 40° C. while creating a vacuum of 100 to 140 hPa. The progress of the reaction is monitored on a silica plate and by HPLC. The aminoether 11 and corresponding cyclized product (I) 12 are formed. The mixture is evaporated to dryness after 48 h. The unpurified product is employed in the following reaction.

$^1$H N.M.R., δ (ppm): 1.95 (s, 3H), 3.1–3.5 (m, 2H), 3.88 (s, 3H), 3.95 (s, 3H), 3.8–4.18 (m, 1H), 4.5–4.8 (m, 1H), 5.22 (s, 1H), 5.60 (d, 1H), 7.30–7.50 (m, 6H), 7.70–7.80 (m, 1H), 8.05–8.35 (m, 3H).

2) 2-Methyl-3-((3S)-9-amino-4-oxo-1-phenyl-3,4,6,7-tetrahydro[1,4]diazepino[6,7,1-*hi*]indol-3-yl)-4-oxo-3,4-dihydroquinazoline-7-carboxylic Acid Methyl Ester (13)

Product 12: 2-Methyl-3-((3S)-9-nitro-4-oxo-1-phenyl-3,4,6,7-tetrahydro[1,4]diazepino[6,7,1-*hi*]indol-3-yl)-4-oxo-3,4-dihydroquinazoline-7-carboxylic Acid Methyl Ester

[(I); A=NO$_2$, Z=CH, Z$^1$=CH, Z$^2$=CH, B=CH$_3$, X$^1$=H, X$^2$=COOCH$_3$ at 7]

The product 11, which can comprise a small amount of 12, is dissolved in 250 ml of trimethyl orthoacetate and 1 g of scandium trifluoromethane-sulphonate is added. Stirring is begun at ambiant temperature (20° C.) and 2 ml of trifluoroacetic acid are added. After 24 h, no more starting material remains. The mixture is evaporated, the residue is taken up in dichloromethane and the solution is washed with a 5% NaHCO$_3$ solution and then with water, dried and evaporated. The residue is purified by chromatography on silica in a gradient of dichloromethane enriched in methanol. 10.47 g of 12 are obtained in the form of crystals from methanol.

$^1$H N.M.R., δ (ppm): 2.72 (s, 3H), 3.1–3.25 (m, 1H), 3.35–3.48 (1H), 3.90 (s, 3H), 4.0–4.12 (m, 1H), 4.68–4.75 (m, 1H), 5.20 (s, 1H), 7.12 (s, 1H), 7.30–7.40 (m, 2H), 7.40–7.50 (m, 3H), 7.97 (d, 1H), 8.10–8.20 (m, 2H), 8.35 (s, 1H), 8.4 (s, 1H).

Product 13:

3.0 g (5.7 mmol) of 12 are dissolved in 150 ml of methanol. The solution is placed in a hydrogenator, into which are poured 3.0 g of 5% ruthenium-on-charcoal and which is brought to a hydrogen pressure of 800 kPa. The interior of the reactor is heated at 80° C. for 1 h. The mixture is examined on a silica plate after cooling: there is no more starting material. The mixture is filtered, the filter residue is rinsed, the filtrate is evaporated and the residue is chromatographed on silica in dichloromethane enriched in methanol. 2 g (yd=71%) of pure product 13 are obtained.

$^1$H N.M.R., δ (ppm): 2.85 (s, 3H), 3.0–3.1 (m, 1H), 3.25–3.35 (m, 1H), 3.6–3.85 (m, 2H), 3.95 (s, 3H), 4.6–4.7 (m, 1H), 6.45 (s, 1H), 6.85 (s, 1H), 5.60 (d, 1H), 7.15 (s, 1H), 7.0–7.6 (m, 5H), 8.0 (d, 1H), 8.25 (d, 1H), 8.45 (s, 1H). I.R.: 3400, 3330, 3220, 1770, 1650, 1620, 1590, 1560, 1480, 1440, 1380, 1300, 1240, 1160, 1090, 1010, 760, 710 cm$^{-1}$. ee=96%.

3) Product 14: (3S)-2-Methyl-3-(9-amino-4-oxo-1-phenyl-3,4,6,7-tetrahydro[1,4]diazepino[6,7,1-*hi*]indol-3-yl)-4-oxo-3,4-dihydroquinazoline-7-carboxylic Acid.

[(I); A=NH$_2$, Z=CH, Z$^1$=CH, Z$^2$=CH, B=CH$_3$, X$^1$=H, X$^2$=CO$_2$H at 7]

4 g of aluminium tribromide are poured into 20 ml of tetrahydrothiophene (THT) and the mixture is cooled to 20° C. After 10 min, 1.4 g of 13, dissolved in 10 ml of THT, are added and the mixture is left stirring overnight at ambiant temperature. Water and dichloromethane are added and a solid is separated. The filtrate is evaporated. The aqueous phase is extracted with dichloromethane and evaporated. All the extracts are combined and brought to a pH of 3.8 in the presence of water and chloroform. Dissolution is carried out in chloroform comprising 15% of methanol. A chromatographic separation is carried out on silica, elution being carried out with a gradient of methanol in dichloromethane.

The fractions comprising the product are combined and subjected to reverse phase chromatography of Kromasil C18 type of 5 μm, elution being carried out with a gradient of acetonitrile in water. Obtained: 0.476 g (Yd=35%) of 14, light beige powder.

T.L.C. (D/MN20): Rf=0.37. ee=94%. $^1$H N.M.R., δ (ppm): 2.7 (s, 3H), 3.0–3.1 (m, 1H), 3.3–3.4 (m, 1H), 3.4–3.7 (m, 3H), 3.8–3.95 (m, 1H), 4.45–4.55 (m, 1H), 6.45 (s, 1H), 6.9 (s, 1H), 6.95 (s, 1H), 7.4–7.6 (m, 5H), 7.95–8.2 (m, 3H). I.R.: 3350, 1680, 1480, 1380, 1300, 1240, 1170, 1110, 1010, 790, 690.

EXAMPLE 3

(3S)-3-(2-Methyl-4-oxo-4H-pyrido[3,4-d]pyrimidin-3-yl)-9-amino-1-phenyl-6,7-dihydro-3H-[1,4]diazepino[6,7,1-*hi*]indol-4-one. (18)

[(I); A=NH$_2$, Z=N, Z$^1$=CH, Z$^2$=CH, B=CH$_3$, X$^1$=H, X$^2$=H]

This synthesis is an illustration of the direct process B, where the synthesis does not start from a protected ortho-amino acid but directly from an ortho-amino acid (V').

1) Synthesis of the Intermediate (II)

Intermediate 15: 2-Amino-N-((3R)-9-nitro-4-oxo-1-phenyl-3,4,6,7-tetrahydro[1,4]diazepino[6,7,1-*hi*]indol-3-yl) nicotinamide.

[(III); A=NO$_2$, Z=N, Z$^1$=CH, Z$^2$=CH, X$^1$=H, X$^2$=H]

3.08 g (22.3 mmol) of 2-aminonicotinic acid are dissolved with stirring in 150 ml of dry dichloromethane in a reactor protected from moisture. 2.51 g (18.6 mmol) of HOBT and 3.83 g (18.6 mmol) of DCC are added. The mixture is cooled to 0° C. and 6.0 g (18.6 mmol) of 1 in 25 ml of dichloromethane are added. After stirring for 24 h at 0° C., the insoluble material is filtered off and the residue is rinsed with dichloromethane. The organic phases are evaporated and the residue is dissolved in an excess of dichloromethane. The organic phase is washed with a 0.1N HKSO$_4$ solution, a saturated NaHCO$_3$ solution and, finally, with water. The solvent is evaporated under vacuum at 0° C. and the residue is purified by flash chromatography on a silica column, elution being carried out with D/M1. 4.0 g of a white crystalline solid 15 are obtained. Yd=48%.

T.L.C. (D/MN5): Rf=0.49. $^1$H N.M.R., δ (ppm): 3.22–3.32 (m, 1H), 3.4–3.55 (m, 1H), 4.05–4.2 (m, 1H), 4.7–4.8 (m, 1H), 5.65 (d, 1H), 6.4 (s, 2H, exchangeable), 6.75 (m, 1H), 7.4–7.5 (m, 2H), 7.5–7.6 (m, 3H), 7.85 (m, 1H), 7.95 (m, 1H), 8.25 (m, 2H), 8.32 (m, 1H).

Intermediate 16: N-[3-((3R)-9-Nitro-4-oxo-1-phenyl-3,4,6,7-tetrahydro[1,4]diazepino[6,7,1-*hi*]indol-3-ylcarbamoyl) pyridin-2-yl]acetimidic Acid Methyl Ester.

[(II); A=NO$_2$, Z=N, Z$^1$=CH, Z$^2$=CH, B=CH$_3$, X$^1$=H, X$^2$=H, R=CH$_3$]

4.0 g of 15 are dissolved in 125 ml of trimethyl orthoacetate; the mixture is heated at 40° C. with stirring under a vacuum of 0.1 kPa in order to remove the methanol which is formed in the reaction. After 6 h, the reaction is complete. The solvent is evaporated and the crude product is used directly in the following reaction.

$^1$H N.M.R., δ (ppm): 2.1 (s, 3H), 3.1–3.6 (m, 2H), 3.95–3.2 (m, 1H), 4.1 (s, 3H), 4.55–4.75 (m, 1H), 5.62 (d, 1H), 7.05–7.2 (m, 1H), 7.25–7.55 (m, 7H), 8.05–8.35 (m, 2H), 8.35–8.55 (m, 1H).

2) (3S)-3-(2-Methyl-4-oxo-4H-pyrido[3,4-d]pyrimidin-3-yl)-9-amino-1-phenyl-6,7-dihydro-3H-[1,4]diazepino[6,7,1-*hi*]indol-4-one. (18)

Product 17:

16 is taken up in 400 ml of dichloromethane, 240 mg (6% by weight) of scandium trifluoromethane-sulphonate are added and the mixture is stirred for 6 h at 40° C. 500 mg of catalyst are again added and the mixture is stirred at normal temperature for 6 h and evaporated to dryness. The residue is taken up in 400 ml of dichloromethane and a further 500 mg of catalyst are added. After 24 h, the reaction is complete. Washing is carried out with water, evaporation is carried out and 5.4 g of crude product are obtained in the form of a resin.

Product 18:

2.6 g (5.6 mmol) of 17 are hydrogenated under a pressure of 800 kPa at 80° C. in 260 ml of methanol for 90 min in the presence of 2.5 g of 5% ruthenium-on-charcoal. The mixture is cooled and filtered through a bed of silica and the organic phase is evaporated. 2.1 g of crude product are obtained, which product is subjected to reverse phase chromatography (5 μm Kromasil C18 column in a linear gradient of acetonitrile in water). 300 mg of product 18 are obtained.

ee=94.5%. $^1$H N.M.R., □ (ppm): 2.7 (s, 3H), 3.05 (m, 1H), 3.3 (m, 1H), 3.9 (q, 1H), 4.5 (t, 1H), 5.4 (s, 2H), 6.4 (s, 1H), 6.85 (s, 1H), 6.9 (s, 1H), 7.5 (m, 5H), 7.9 (d, 1H), 8.7 (d, 1H), 9.1 (s, 1H).

EXAMPLE 4

(3S)-3-(2-Methyl-4-oxo-4H-quinazolin-3-yl)-9-methyl-1-phenyl-6,7-dihydro-3H-[1,4]diazepino[6,7,1-hi]indol-4-one. (23)

[(I); A=CH$_3$, Z=CH, Z$^1$=CH, Z$^2$=CH, B=CH$_3$, X$^1$=H, X$^2$=H]

1) Synthesis of the Intermediate (II)

Intermediate (19): (3R)-3-Amino-9-methyl-1-phenyl-6,7-dihydro-3H-[1,4]diazepino[6,7,1-hi]indol-4-one. [(VI); A=CH$_3$].

A method for the preparation of this product is disclosed in Application WO 96/11690.

Intermediate (20): [2-((3R)(9-Methyl-4-oxo-1-phenyl-3,4,6,7-tetrahydro[1,4]diazepino[6,7,1-hi]indol-3-ylcarbamoyl)phenyl]carbamic Acid t-Butyl Ester.

[(IV); A=CH$_3$, Z=CH, Z$^1$=CH, Z$^2$=CH, X$^1$=H, X$^2$=H, PG=t-BOC].

4.07 g (17.61 mmol) of 2 are dissolved with stirring in 65 ml of dry dichloromethane in a reactor protected from moisture. The mixture is cooled to 0° C. and 5 g (17.61 mmol) of 19 in 65 ml of dichloromethane are added. 2.32 g (17.61 mmol) of HOBT and 3.54 g (17.61 mmol) of DCC are added. After stirring for 2 h at 0° C., it is confirmed by T.L.C. (eluant: D/M 5) that no more 19 remains. The solvent is evaporated under vacuum at 20° C. and the residue is purified by flash chromatography on a silica column, elution being carried out with the solvent dichloromethane/2% acetone. 7.4 g of a white crystalline solid are obtained.

Yd=82%. T.L.C. (D/M5): Rf=0.76; H.P.L.C. (Pirkle column, D-phenylglycine, eluant hexane/ethanol 50/50, T=30° C.; flow rate: 1 ml/min, UV: 254 nm): ee=97%. [α]$_D$=+27.50 (c=0.0204 g/ml, acetone, Na-D 589 nm); $^1$H N.M.R., δ (ppm): 1.4 (s, 9H), 2.3 (s, 3H), 3.1 (m, 1H), 3.35 (m, 1H), 3.9 (m, 1H), 4.5 (m, 1H), 5.45 (d, 1H), 7.0 (s, 1H), 7.10 (t, 1H), 7.5 (m, 7H), 8.1 (d, 1H), 8.22 (d, 1H), 9.8 (d, 1H), 10.4 (s, 1H).

Intermediate 21: 2-Amino-N-((3R)-9-methyl-4-oxo-1-phenyl-3,4,6,7-tetrahydro[1,4]diazepino[6,7,1-hi]indol-3-yl)benzamide.

[(III); A=CH$_3$, Z=CH, Z$^1$=CH, Z$^2$=CH, X$^1$=H, X$^2$=H].

7.4 g (145 mmol) of 20 are introduced into 400 ml of dichloromethane in a 100 ml reactor protected from moisture and under a nitrogen atmosphere and then 57.84 g (507.25 mmol) of trifluoroacetic acid are introduced at 0° C. The mixture is stirred for 1 h at 0° C. and is evaporated at 20° C. under vacuum. The residue is taken up in dichloromethane and the organic solution is washed with an aqueous NaHCO$_3$ solution and then with an NaCl solution and evaporated at 20° C. Crude product: 5 g. The residue is purified by flash chromatography on a silica column, elution being carried out with a solvent dichloromethane/5% acetone. 4.75 g of a white powder 21 are obtained. Yd=80%.

Chiral HPLC (Pirkle column, D-phenylglycine, eluant hexane/ethanol 50/50, T=30° C., flow rate: 1 ml/min, UV: 254 nm): ee=98%. T.L.C. (D/M5): Rf=0.23. [α]$_D$=+36.820 (c=0.0315 g/ml, acetone, Na-D 589 nm). $^1$H N.M.R., δ (ppm): 2.3 (s, 3H), 3.1 (m, 1H), 3.3 (m, 1H), 3.9 (m, 1H), 4.5 (m, 1H), 5.4 (d, 1H), 6.35 (m, 1H), 6.55 (t, 1H), 6.7 (d, 1H), 7.0 (s, 1H), 7.2 (t, 1H), 7.4 (m, 6H), 7.8 (d, 1H), 9.15 (d, 1H).

Intermediate 22: N-[2-((3R)-9-Methyl-4-oxo-1-phenyl-3,4,6,7-tetrahydro[1,4]diazepino[6,7,1-hi]indol-3-ylcarbamoyl)phenyl]acetimidic Acid Methyl Ester

[(II); A=CH$_3$, Z=CH, Z$^1$=CH, Z$^2$=CH, B=CH$_3$, X$^1$=H, X$^2$=H, R=CH$_3$].

300 ml of trimethyl orthoacetate and 4.5 g (11 mmol) of 21 are introduced into a reactor protected from moisture and under a nitrogen atmosphere. The stirred reactor is placed under a vacuum of 0.1 kPa and is heated at 40° C. for 6 h. Evaporation is carried out under vacuum; NMR confirms the existence of a new product 22. Crude product: 5.55 g. The product is employed as is in the following stage.

Chiral HPLC (Pirkle column, D-phenylglycine, eluant hexane/ethanol 50/50, T=30° C., flow rate: 1 ml/min, UV: 254 nm): ee=99%. T.L.C. (D/M5): Rf=0.19.

2) (3S)-3-(2-Methyl-4-oxo-4H-quinazolin-3-yl)-9-methyl-1-phenyl-6,7-dihydro-3H-[1,4]diazepino[6,7,1-hi]indol-4-one. (23)

300 ml of dichloromethane and 5.55 g of 22 are introduced into a reactor protected from moisture and under a nitrogen atmosphere. 0.117 g of scandium trifluoromethane-sulphonate is added and the mixture is left stirring for 28 h at ambiant temperature (18° C.). Washing is carried out with an NaHCO$_3$ solution, drying is carried out and evaporation is carried out. The residue is chromatographed on silica, elution being carried out with a gradient of acetone in dichloromethane. 0.65 g of the product 23 is obtained.

Chiral HPLC (Pirkle column, D-phenylglycine, eluant: hexane/ethanol 50/50, T=30° C., flow rate 1 ml/min, UV: 254 nm): ee=99%. T.L.C. (D/M5): Rf=0.23. $^1$H N.M.R., δ (ppm): 2.35 (s, 3H), 3.1 (m, 1H), 3.3 (m, 1H), 3.95 (m, 1H), 4.7 (m, 1H), 7.0–7.80 (m, 12H), 8.20 (s, 1H).

EXAMPLE 5

(3S)-9-Methoxy-3-(2-methyl-4-oxo-4H-quinazolin-3-yl)-1-phenyl-6,7-dihydro-3H-1,4diazepino[6,7,1-hi]indol-4-one. (28)

[(I); A=OCH$_3$, Z=CH, Z$^1$=CH, Z$^2$=CH, B=CH$_3$, X$^1$=H, X$^2$=H]

1) Synthesis of the Intermediate (II)

Intermediate 24: (3R)-3-Amino-9-methoxy-1-phenyl-6,7-dihydro-3H-[1,4]diazepino[6,7,1-hi]indol-4-one. [(VI); A=OCH$_3$].

7.1 g (231 mmol) of (3R,S)-3-amino-9-methoxy-1-phenyl-6,7-dihydro-3H-[1,4]diazepino[6,7,1-hi]indol-4-one, prepared as taught in Patent Application WO 96/11690, are brought to reflux in 17.75 ml of acetonitrile; 8.92 g (23.1 mmol) of di(p-toluoyl)-D-tartaric acid, brought beforehand to reflux in 17.75 ml of acetonitrile, are added thereto. The addition with stirring is carried out very rapidly. Reflux is maintained for 5 min before the mixture is left standing for 18 h. The precipitate is filtered off, rinsed with 35 ml of acetonitrile and dried under 0.1 kPa at 35° C. 8.5 g of salt are obtained, which salt is taken up in 85 ml of acetonitrile;

it is brought to reflux for 5 min and left standing for at least 4 h. The precipitate is filtered off, rinsed with 40 ml of acetonitrile and dried under 0.1 kPa at 35° C. 5 g of salt are obtained. The base is released, by taking 5 g of salt up in 100 ml of a molar sodium hydroxide solution cooled beforehand to 0° C., and then extraction is carried out with 3 times 200 ml of isopropyl acetate. The organic phase is washed with a saturated NaCl solution, dried over sodium sulphate and evaporated. 2.2 g of intermediate 24 are obtained.

Chiral HPLC (Pirkle column, D-phenylglycine, eluant: hexane/isopropanol 50/50, T=20° C., flow rate: 1.2 ml/min, UV: 254 nm): ee=99%.
Preparation of the sample for chiral HPLC: the product must be derivatized with 2 equivalents of p-tolyl isocyanate in dichloromethane and then diluted in isopropanol to 0.5 mg/ml before being injected.

Intermediate 25: [2-((3R)-(9-Methoxy-4-oxo-1-phenyl-3,4, 6,7-tetrahydro[1,4]diazepino[6,7,1-*hi*]indol-3-ylcarbamoyl)phenyl]carbamic Acid t-Butyl Ester.
[(IV); A=$OCH_3$, Z=CH, $Z^1$=CH, $Z^2$=CH, $X^1$=H, $X^2$=H, PG=t-BOC].

1.7 g (7.16 mmol) of 2 are dissolved with stirring in 55 ml of dry dichloromethane in a reactor protected from moisture. The mixture is cooled to 0° C. and 2.2 g (7.16 mmol) of 24 in 55 ml of dichloromethane are added. 0.97 g (7.16 mmol) of HOBT and 1.47 g (7.16 mmol) of DCC are added. After stirring for 8 h at 0° C. and then overnight at ambiant temperature, it is confirmed by T.L.C. (eluant: D/M5) that no more 24 remains. The solvent is evaporated under vacuum at 30° C. and the residue is purified by flash chromatography on a silica column, elution being carried out with the solvent dichloromethane/3% acetone. 3.2 g of a white crystalline solid 25 are obtained. Yd=85%

T.L.C. (D/M5): Rf=0.72. H.P.L.C. (Pirkle column, D-phenylglycine, eluant hexane/ethanol 50/50, T=30° C.; flow rate: 1 ml/min, UV: 254 nm): ee=98%. $[\alpha]_D$=+11° (c=0.04507 g/ml, acetone, Na-D 589 nm); $^1$H N.M.R., δ (ppm): 1.45 (s, 9H), 3.1 (m, 1H), 3.4 (m, 1H), 3.7 (s, 3H), 3.9 (m, 1H), 4.5 (m, 1H), 5.5 (d, 1H), 6.65 (s, 1H), 7.10 (t, 1H), 7.3 (s, 1H), 7.5 (m, 6H), 8.25 (d, 1H), 9.8 (d, 1H), 10.4 (s, 1H).

Intermediate 26: 2-Amino-N-((3R)-9-methoxy-4-oxo-1-phenyl-3,4,6,7-tetrahydro[1,4]diazepino[6,7,1-*hi*]indol-3-yl)benzamide.
[(III); A=$OCH_3$, Z=CH, $Z^1$=CH, $Z^2$=CH, $X^1$=H, $X^2$=H].

3.1 g (5.88 mmol) of 25 are introduced into 260 ml of dichloromethane in a 500 ml reactor protected from moisture and under a nitrogen atmosphere and then 23.53 g (20.604 mmol) of trifluoroacetic acid are introduced at 0° C. The mixture is stirred for 1 h at 0° C. and is evaporated at 20° C. under vacuum. The residue is taken up in dichloromethane and the organic solution is washed with an $NaHCO_3$ solution and then with an NaCl solution and evaporated at 20° C. 2.75 g of pure 26 are obtained.

The product is employed as is in the following stage.

Chiral HPLC (Pirkle column, D-phenylglycine, eluant hexane/ethanol 50/50, T=30° C., flow rate: 1 ml/min, UV: 254 nm): ee=99%. T.L.C. (D/M5): Rf=0.20. $[\alpha]_D$=+20.5° (c=0.02923 g/ml, acetone, Na-D 589 nm). $^1$H N.M.R., δ (ppm): 3.15 (m, 1H), 3.45 (m, 1H), 3.7 (s, 3H), 3.9 (m, 1H), 4.5 (m, 1H), 5.45 (d, 1H), 6.4 (m, 1H), 6.55 (t, 1H), 6.65 (s, 1H), 6.7 (d, 1H), 7.3 (s, 1H), 7.55 (m, 5H), 7.8 (d, 1H), 9.10 (d, 1H).

Intermediate 27: N-[2-((3R)-9-Methoxy-4-oxo-1-phenyl-3, 4,6,7-tetrahydro[1,4]diazepino[6,7,1-*hi*]indol-3-ylcarbamoyl)phenyl]acetimidic Acid Methyl Ester
[(II); A=$OCH_3$, Z=CH, $Z^1$=CH, $Z^2$=CH, B=$CH_3$, $X^1$=H, $X^2$=H, R=$CH_3$].

200 ml of trimethyl orthoacetate and 2.5 g (5.86 mmol) of 26 are introduced into a reactor protected from moisture and under a nitrogen atmosphere. The stirred reactor is placed under a vacuum of 0.1 kPa and is heated at 40° C. for 6 h. Evaporation is carried out under vacuum. NMR confirms the existence of the new product 27 and the presence of traces of the starting material 26.

Crude product: 2.5 g. The product is employed as is in the following stage.

Chiral HPLC (Pirkle column, D-phenylglycine, eluant hexane/ethanol 50/50, T=30° C., flow rate 1 ml/min, UV: 254 nm): ee=99%. T.L.C. (D/M5): Rf=0.22.

2) (3S)-9-Methoxy-3-(2-methyl-4-oxo-4H-quinazolin-3-yl)-1-phenyl-6,7-dihydro-3H-[1,4]diazepino[6,7,1-*hi*]indol-4-one. (28)

200 ml of dichloromethane and 2.5 g of 27 are introduced into a reactor protected from moisture and under a nitrogen atmosphere. 0.051 g of scandium trifluoromethanesulphonate is added and the mixture is left stirring for 36 h at ambiant temperature (18° C.). Washing is carried out with an $NaHCO_3$ solution, drying is carried out and evaporation is carried out. The residue is chromatographed on silica, elution being carried out with a gradient of acetone in dichloromethane. 1.7 g of a pure product 28 are obtained.

Chiral HPLC (Pirkle column, D-phenylglycine, eluant: hexane/ethanol 50/50, T=30° C., flow rate: 1 ml/min, UV: 254 nm): ee=99%. T.L.C. (D/M5): Rf=0.20. $^1$H N.M.R., δ (ppm): 2.8 (s, 3H), 3.1 (m, 1H), 3.4 (m, 1H), 3.75 (m, 1H), 3.9 (m, 1H), 4.7 (d, 1H), 6.70 (m, 1H), 7.10 (s, 1H), 7.2 (s, 1H), 7.3–7.85 (m, 8H), 8.2 (d 1H).

EXAMPLE 6

Synthesis of the Compound 12 [(I): A=$NO_2$, Z= CH, $Z^1$=CH, $Z^2$=CH, B=$CH_3$, $X^1$=H, $X^2$=$COOCH_3$ in 7] From the Intermediate 10 [(III): A=$NO_2$, Z= CH, $Z^1$=CH, $Z^2$=CH, $X^1$=H, $X^2$=para-$CO_2CH_3$] in the Presence of Various Catalysts 2.8 g of product 10 are dissolved in 50 ml of trimethyl orthoacetate and are left for 24 hours at ambient temperature. Thin layer chromatography makes it possible to confirm that little starting material remains. The formation of a small amount of imines is also observed. 100 mg of catalyst are subsequently added all at once to 2 ml of solution (which corresponds to 112 mg of starting material). This reaction is carried out with 6 different catalysts. A catalyst-free reaction is also carried out. The progress of the reaction is monitored by thin layer chromatography (eluent D/M1,5).

After 48 hours, each reaction medium is taken up in 100 ml of methylene chloride. After adding 1N HCl and dissolving the catalyst, the following operations are carried out: separating by settling, washing with $NaHCO_3$, drying and evaporating. The product obtained is finally weighed.

1 mg/ml solutions of the various products are prepared and then the products are analysed by analytical HPLC using the following methods:
1) column of C18 Kromasil 5 □m type (250□4.6 mm), elution being carried out with a gradient of acetonitrile in water.
   $t_{0\ min}$: 20% acetonitrile,
   $t_{25\ min}$: 95% acetonitrile).
2) column of Pirckle D-phenylglycine type (250□4.6 mm), elution being carried out with a hexane/ethanol (50/50) mixture.

The retention times for the two optical isomers are 10.15 min for the R enantiomer and 14.60 min for the S enantiomer.

Results:

| Catalyst used | Mass of product obtained | % of cyclized product (12) | Optical purity | By-products | Un-cyclized product |
|---|---|---|---|---|---|
| Catalyst-free control | 106 mg | 0% | >98% | | 99% |
| Sc(OSO₂CF₃)₃ | 106 mg | 92% | >98% | 5% | 0% |
| AlBr₃ | 98 mg | 10% | complete epimerization | 83% | 0% |
| AlCl₃ | 110 mg | 44% | >98% | 30% | 0% |
| BF₃ | 130 mg | 26% | >98% | 64% | 1% |
| ZnCl₂ | 120 mg | 76% | >98% | 20% | 0% |
| CF₃COOH | 105 mg | 22% | >98% | 47% | 28% |

What is claimed is:

1. A process for the preparation of a diazepinoindolone of formula

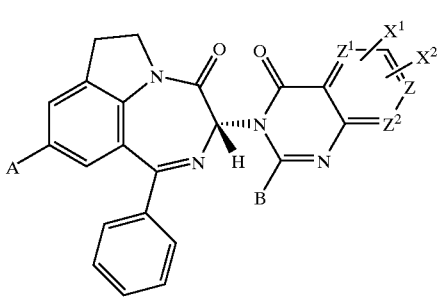

(I)

in which:
A is hydrogen, $C_1$–$C_4$ alkyl, hydroxyl, $C_1$–$C_4$ alkoxy, nitro, cyano or $NR^1R^2$; $R^1$ and $R^2$ are independently hydrogen or $C_1$–$C_4$ alkyl or form, together with the nitrogen atom to which they are bonded, a ring having 4 or 5 carbon atoms;
B is hydrogen or $C_1$–$C_4$ alkyl;
Z is CH and $Z^1$ and $Z^2$ are together CH or N; or Z is N and $Z^1$ and $Z^2$ are CH;
$X^1$ and $X^2$ are independently hydrogen, $C_1$–$C_4$ alkyl, —(CH$_2$)$_j$—OR$^3$, halogen, cyano, —O—(C$_1$–C$_6$ alkyl), —C(=O)R$^4$, —C(=O)OR$^5$, —C(=O)NR$^6$R$^7$, or

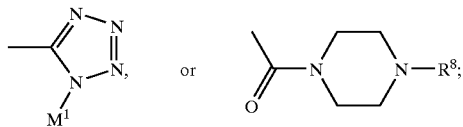

$R^3$, $R^4$ and $R^5$ are independently hydrogen, $C_1$–$C_6$ alkyl, benzyl, phenethyl or —$Q^1$—$Q^2$;
$R^6$ is hydrogen or $C_1$–$C_4$ alkyl;
$R^7$ is hydrogen, $C_1$–$C_4$ alkyl, —CHR$^A$—C(=O)OM$^2$ or —$Q^3$—$Q^4$;
$R^8$ is hydrogen, $C_1$–$C_4$ alkyl or —$Q^5$—$Q^6$;
$R^A$ is a natural α-amino acid residue, the carbon atom to which it is bonded being able to have either the S configuration or the R configuration;
$Q^1$ is —(CH$_2$)$_k$—(CHOH)$_m$—(CH$_2$)$_p$—;
$Q^2$ is hydroxyl, —O—(C$_1$–C$_6$ alkyl), —OC(=O)—(C$_1$–C$_6$ alkyl) or 4-morpholinyl;
$Q^3$ and $Q^5$ are independently a bond, —CH$_2$—, —(CH$_2$)$_2$— or —(CH$_2$)$_3$—;
$Q^4$ is —NM$^3$M$^4$ or 4-morpholinyl;
$Q^6$ is —M$^5$ or —OM$^6$;
$M^1$, $M^2$, $M^3$, $M^4$, $M^5$ and $M^6$ are independently hydrogen or $C_1$–$C_4$ alkyl;
j is 1, 2 or 3; k is 1, 2 or 3;
m is 0, 1, 2, 3 or 4; p is 0, 1, 2 or 3, with the proviso that, if m>0, then p>0;
which comprises the intramolecular cyclization at a temperature not higher than 40° C. of a product of formula

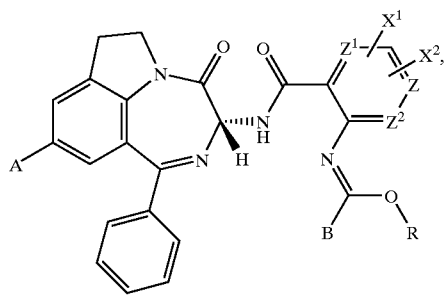

in which A, Z, $Z^1$, $Z^2$, B, $X^1$ and $X^2$ have the meaning defined above and R is $C_1$–$C_4$ alkyl, in the presence of a weak Lewis acid catalyst selected from scandium trifluoromethanesulphonate; aluminium trifluoromethanesulphonate; lanthanide; silicon, magnesium, tin(II), copper(II), zinc or silver trifluoromethanesulphonates; dimethoxydicyclopentadienyltitanium(IV); dicyclopentadienyltitanium(IV); bis(trifluoromethanesulphonate); iron(III), aluminium or zinc acetylacetonate; zinc diacetonate; dimthoxymagnesium; triisopropoxyaluminium; tetrabutoxytitanium(IV); tetraisopropoxytitanium(IV); trimethylboron; triethylaluminium, diethylzinc; triisobutylaluminium; tetrabutyltin(IV); triphenylboron; triphenylantimony; zinc, tin(II), antimony, titanium, scandium, indium, gallium or mercury(II) halides.

2. The process of claim 1, in which the weak Lewis acid is scandium trifluoromethanesulphonate.

3. The process of claim 1, comprising the additional step of reducing a compound of formula (I) in which A is —NO$_2$, to form a compound of formula (I) in which A is —NH$_2$.

4. The process of claim 1, wherein A is —NH$_2$, B is CH$_3$, and $X^1$ and $X^2$ are independently hydrogen, halogen or —C(=O)OR$^5$.

* * * * *